US007790152B2

(12) United States Patent
Kosaka et al.

(10) Patent No.: US 7,790,152 B2
(45) Date of Patent: *Sep. 7, 2010

(54) ENHANCER FOR ANTIBODY TO LYMPHOCYTIC TUMORS

(75) Inventors: Masaaki Kosaka, Tokushima (JP); Yasuo Koishihara, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1516 days.

This patent is subject to a terminal disclaimer.

(21) Appl. No.: 10/428,085

(22) Filed: May 2, 2003

(65) Prior Publication Data

US 2003/0175281 A1   Sep. 18, 2003

Related U.S. Application Data

(63) Continuation of application No. 09/509,530, filed as application No. PCT/JP98/04645 on Oct. 14, 1998, now abandoned.

(30) Foreign Application Priority Data

Oct. 14, 1997 (JP) ................................. 9-280759
Aug. 5, 1998 (JP) ................................ 10-222024

(51) Int. Cl.
*A61K 45/00* (2006.01)
*A61K 39/395* (2006.01)

(52) U.S. Cl. .................. 424/85.1; 424/85.2; 424/133.1; 424/139.1; 424/141.1; 424/153.1; 424/154.1; 424/155.1

(58) Field of Classification Search ........................ None
See application file for complete search history.

(56) References Cited

U.S. PATENT DOCUMENTS

| 4,401,756 | A | * | 8/1983 | Gillis | ......................... 435/70.4 |
| 5,328,989 | A | * | 7/1994 | Vellekamp et al. | .......... 530/351 |
| 5,756,318 | A | | 5/1998 | Kosuna | |
| 5,830,463 | A | | 11/1998 | Duke et al. | |
| 6,180,370 | B1 | | 1/2001 | Queen et al. | |
| 6,258,352 | B1 | * | 7/2001 | Shimonaka | ................. 424/85.2 |

FOREIGN PATENT DOCUMENTS

| EP | 0 256 714 A2 | 2/1988 |
| EP | 0 960 936 A1 | 12/1999 |
| WO | WO 96/04925 | 2/1996 |

OTHER PUBLICATIONS

Clark (Protein Engineering of Antibody Molecules for Prophylactic and Therapeutic Applications in Man, 1993, pp. 1).*
Schlom ('Monoclonal antibodies; They're More and Less Than You Think', In: Molecular Foundations of Oncology, .1991, pp. 95-134).*
Abstract of Hanton et al (Annales de Recherches Veterinaires, 1984, vol. 15, pp. 443-454).*
Kay, Neil K., "Restoration of Impaired Natural Killer Cell Activity of B-Chronic Lymphocytic Leukemia Patients by Recombinant Interleukin-2", American Journal of Hematology, vol. 24, No. 2, 1987, pp. 161-167.
Parkinson, David R., "Present Status of Biological Response Modifiers in Cancer", American Journal of Medicine, vol. 99, No. 6, Part A, 1995, pp. 54S-56S.
Pawelec, G., et al., "Partial Correction of Defective Generation of Lymphokine-Activator Killer Cells in Patients with Chronic Myelogenous Leukemia After", Cancer Immunology Immunotherapy, vol. 29, No. 1, 1989, pp. 63-66.
Peest, Dietrich et al., "Low Dose Recombinant Interleukin-2 Therapy in Advanced Multiple Myeloma", British Journal of Haematology, 1995, vol. 89, No. 2, pp. 328-337.
Vachino, Gloria et al., "Complement Activation in Cancer Patients Undergoing Immunotherapy With Interleukin-2 (IL-2): Binding of Compelement and C-Reactive Protein by IL-2—Activated Lymphocytes", Blood, 1991, vol. 78, No. 10, pp. 2503-2513.
Stewart, A. K. et al., "Immunogene Therapy with Interleukin 12 (IL-12), B7-1 and Flt3 Ligand (Flt3L) in a Murine Myeloma Model: IL-12 and B7-1 Expressing Cells Confer Protective Immunity", Blood, 1997, vol. 90, No. 10, Suppl1, Part 1, pp. 358A-359A.
Ozaki et al., "Localization and Imaging of Human Plasmacytoma Xenografts in Severe Combined Immunodeficiency Mice by a New Murine Monoclonal Antibody, Anti-HM1.24," *Tokushima J. exp. Med.* vol. 43, pp. 7-15, (1996).
Goto et al., "A Novel Membrane Antigen Selectively Expressed on Terminally Differentiated Human B Cells," *Blood*, vol. 84, No. 6, pp. 1922-1930, (1994).
Ozaki et al., "Immunotherapy of Multiple Myeloma With a Monoclonal Antibody Directed Against a Plasma Cell-Specific Antigen, HM1.24," *Blood*, vol. 90, No. 8, pp. 3179-3186, (1997).
Ishikawa et al., *Genomics*, vol. 26, pp. 527-534, (1995).
Gill et al., *Cancer Research*, vol. 49, pp. 5377-5379, (1989).
Ottonello et al., *Blood*, vol. 87, pp. 5171-5178, (1996).
Hird et al., *Genes and Cancer*, (Monograph), pp. 183-189, (1990).
Evans et al., *Cellular Immunology*, vol. 179, pp. 66-73, (1997).
Takeuchi et al., *Japanese Journal of Cancer Research*, vol. 87, pp. 1251-1258, (1996).
Mihich et al., *Seminars in Oncology*, vol. 13, pp. 234-254, (1986).
Eisenthal et al., "Systemic Induction of Cells Mediating Antibody-dependent Cellular Cytotoxicity following Administration of Interleukin 2," Cancer Research, Dec. 15, 1989, 49:6953-6959.

* cited by examiner

*Primary Examiner*—Karen A Canella
(74) *Attorney, Agent, or Firm*—Foley & Lardner LLP (57) ABSTRACT

An enhancer, for treatment of lymphocytic tumors, of an antibody that specifically binds to protein having the amino acid sequence as set forth in SEQ ID NO: 1 and that has a cytotoxic activity, said enhancer comprising a biological response modifier as an active ingredient.

8 Claims, 3 Drawing Sheets

Fig.1

SEQUENCE LISTING

<160> NUMBER OF SEQ ID NOS: 8

<210> SEQ ID NO 1
<211> LENGTH: 1013
<212> TYPE: DNA
<213> ORGANISM: Homo sapiens
<220> FEATURE:
<221> NAME/KEY: CDS
<222> LOCATION: (23)..(562)

<400> SEQUENCE: 1

```
gaattcggca cgagggatct gg atg gca tct act tcg tat gac tat tgc aga        52
                         Met Ala Ser Thr Ser Tyr Asp Tyr Cys Arg
                           1               5                  10 gtg ccc atg gaa gac ggg gat aag cgc tgt aag ctt ctg ctg ggg ata        100
Val Pro Met Glu Asp Gly Asp Lys Arg Cys Lys Leu Leu Leu Gly Ile
             15                  20                  25 gga att ctg gtg ctc ctg atc atc gtg att ctg ggg gtg ccc ttg att       148
Gly Ile Leu Val Leu Leu Ile Ile Val Ile Leu Gly Val Pro Leu Ile
         30                  35                  40 atc ttc acc atc aag gcc aac agc gag gcc tgc cgg gac ggc ctt cgg        196
Ile Phe Thr Ile Lys Ala Asn Ser Glu Ala Cys Arg Asp Gly Leu Arg
             45                  50                  55 gca gtg atg gag tgt cgc aat gtc acc cat ctc ctg caa caa gag ctg        244
Ala Val Met Glu Cys Arg Asn Val Thr His Leu Leu Gln Gln Glu Leu
 60                  65                  70 acc gag gcc cag aag ggc ttt cag gat gtg gag gcc cag gcc gcc acc        292
Thr Glu Ala Gln Lys Gly Phe Gln Asp Val Glu Ala Gln Ala Ala Thr
 75                  80                  85                  90 tgc aac cac act gtg atg gcc cta atg gct tcc ctg gat gca gag aag        340
Cys Asn His Thr Val Met Ala Leu Met Ala Ser Leu Asp Ala Glu Lys
                 95                 100                 105 gcc caa gga caa aag aaa gtg gag gag ctt gag gga gag atc act aca        388
Ala Gln Gly Gln Lys Lys Val Glu Glu Leu Glu Gly Glu Ile Thr Thr
            110                 115                 120 tta aac cat aag ctt cag gac gcg tct gca gag gtg gag cga ctg aga        436
Leu Asn His Lys Leu Gln Asp Ala Ser Ala Glu Val Glu Arg Leu Arg
        125                 130                 135 aga gaa aac cag gtc tta agc gtg aga atc gcg gac aag aag tac tac        484
Arg Glu Asn Gln Val Leu Ser Val Arg Ile Ala Asp Lys Lys Tyr Tyr
    140                 145                 150 ccc agc tcc cag gac tcc agc tcc gct gcg gcg ccc cag ctg ctg att        532
Pro Ser Ser Gln Asp Ser Ser Ser Ala Ala Ala Pro Gln Leu Leu Ile
155                 160                 165                 170 gtg ctg ctg ggc ctc agc gct ctg ctg cag tgagatccca ggaagctggc        582
Val Leu Leu Gly Leu Ser Ala Leu Leu Gln
                175                 180 acatcttgga aggtccgtcc tgctcggctt ttcgcttgaa cattcccttg atctcatcag    642
ttctgagcgg gtcatgggcc aacacggtta gcggggagag cacggggtag ccggagaagg    702
gcctctggag caggtctgga ggggccatgg ggcagtcctg ggtgtgggga cacagtcggg    762
ttgacccagg gctgtctccc tccagagcct ccctccggac aatgagtccc cctcttgtc     822 tcccaccctg agattgggca tggggtgcgg tgtgggggc atgtgctgcc tgttgttatg    882
ggtttttttt gcggggggggg ttgctttttt ctggggtctt tgagctccaa aaaaataaac   942
acttcctttg agggagagca cacccttaaaa aaaaaaaaaa aaaaaaaaaa aaaaaattc    1002 gggcggccgc c                                                        1013
```

<210> SEQ ID NO 2
<211> LENGTH: 379
<212> TYPE: DNA
<213> ORGANISM: Artificial Sequence
<220> FEATURE:
<223> OTHER INFORMATION: Description of Artificial Sequence: L chain V
      region version a of humanized anti-HM1.24 antibody
<220> FEATURE:
<221> NAME/KEY: sig_peptide
<222> LOCATION: (1)..(57)
<220> FEATURE:
<221> NAME/KEY: mat_peptide
<222> LOCATION: (58)..(378)
<220> FEATURE:
<221> NAME/KEY: CDS
<222> LOCATION: (1)..(378)

<400> SEQUENCE: 2

```
atg gga tgg agc tgt atc atc ctc tcc ttg gta gca aca gct aca ggt      48
Met Gly Trp Ser Cys Ile Ile Leu Ser Leu Val Ala Thr Ala Thr Gly
            -15                 -10                 -5 gtc cac tcc gac atc cag atg acc cag agc cca agc agc ctg agc gcc      96
Val His Ser Asp Ile Gln Met Thr Gln Ser Pro Ser Ser Leu Ser Ala
     -1   1                   5                  10 agc gtg ggt gac aga gtg acc atc acc tgt aag gct agt cag gat gtg     144
Ser Val Gly Asp Arg Val Thr Ile Thr Cys Lys Ala Ser Gln Asp Val
         15                  20                  25 aat act gct gta gcc tgg tac cag cag aag cca gga aag gct cca aag     192
Asn Thr Ala Val Ala Trp Tyr Gln Gln Lys Pro Gly Lys Ala Pro Lys
 30                  35                  40                  45 ctg ctg atc tac tcg gca tcc aac cgg tac act ggt gtg cca agc aga     240
Leu Leu Ile Tyr Ser Ala Ser Asn Arg Tyr Thr Gly Val Pro Ser Arg
                 50                  55                  60 ttc agc ggt agc ggt agc ggt acc gac ttc acc ttc acc atc agc agc     288
Phe Ser Gly Ser Gly Ser Gly Thr Asp Phe Thr Phe Thr Ile Ser Ser
             65                  70                  75 ctc cag cca gag gac atc gct acc tac tac tgc cag caa cat tat agt     336
Leu Gln Pro Glu Asp Ile Ala Thr Tyr Tyr Cys Gln Gln His Tyr Ser
         80                  85                  90 act cca ttc acg ttc ggc caa ggg acc aag gtg gaa atc aaa c            379
Thr Pro Phe Thr Phe Gly Gln Gly Thr Lys Val Glu Ile Lys
     95                 100                 105
```

<210> SEQ ID NO 3
<211> LENGTH: 418
<212> TYPE: DNA
<213> ORGANISM: Artificial Sequence
<220> FEATURE:
<223> OTHER INFORMATION: Description of Artificial Sequence: H chain V
      region version r of humanized anti-HM1.24 antibody
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)
<220> FEATURE:
<221> NAME/KEY: CDS
<222> LOCATION: (1)..(417)

<400> SEQUENCE: 3

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
     -1   1                   5                  10
```

```
cct ggg gcc tca gtg aag gtt tcc tgc aag gca tct gga tac acc ttc      144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt      192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt      240
Glu Trp Met Gly Ser Ile Phe Pro Gly Asp Gly Asp Thr Arg Tyr Ser
                 50                  55                  60 cag aag ttc aag ggc aga gtc acc atg acc gca gac aag tcc acg agc      288
Gln Lys Phe Lys Gly Arg Val Thr Met Thr Ala Asp Lys Ser Thr Ser
             65                  70                  75 aca gcc tac atg gag ctg agc agc ctg aga tct gag gac acg gcc gtg      336
Thr Ala Tyr Met Glu Leu Ser Ser Leu Arg Ser Glu Asp Thr Ala Val
         80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
 95                 100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 4
<211> LENGTH: 418
<212> TYPE: DNA
<213> ORGANISM: Artificial Sequence
<220> FEATURE:
<223> OTHER INFORMATION: Description of Artificial Sequence: H chain V
      region version s of humanized anti-HM1.24 antibody
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)
<220> FEATURE:
<221> NAME/KEY: CDS
<222> LOCATION: (1)..(417)

<400> SEQUENCE: 4 atg gac tgg acc tgg agg gtc ttc ttc ttg ctg gct gta gct cca ggt       48
Met Asp Trp Thr Trp Arg Val Phe Phe Leu Leu Ala Val Ala Pro Gly
                -15                 -10                  -5 gct cac tcc cag gtg cag ctg gtg cag tct ggg gct gag gtg aag aag       96
Ala His Ser Gln Val Gln Leu Val Gln Ser Gly Ala Glu Val Lys Lys
         -1   1                   5                  10 cct ggg gcc tca gtg aag gtt tcc tgc aag gca tct gga tac acc ttc      144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt      192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt      240
Glu Trp Met Gly Ser Ile Phe Pro Gly Asp Gly Asp Thr Arg Tyr Ser
                 50                  55                  60 cag aag ttc aag ggc aga gtc acc atc acc gca gac aag tcc acg agc      288
Gln Lys Phe Lys Gly Arg Val Thr Ile Thr Ala Asp Lys Ser Thr Ser
             65                  70                  75 aca gcc tac atg gag ctg agc agc ctg aga tct gag gac acg gcc gtg      336
Thr Ala Tyr Met Glu Leu Ser Ser Leu Arg Ser Glu Asp Thr Ala Val
         80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
```

```
                95                 100                 105
tgg ggg caa ggg acc acg gtc acc gtc tcc tca g                          418
Trp Gly Gln Gly Thr Thr Val Thr Val Ser Ser
110                 115                 120

<210> SEQ ID NO 5
<211> LENGTH: 180
<212> TYPE: PRT
<213> ORGANISM: Homo sapiens

<400> SEQUENCE: 5

Met Ala Ser Thr Ser Tyr Asp Tyr Cys Arg Val Pro Met Glu Asp Gly
  1               5                  10                  15

Asp Lys Arg Cys Lys Leu Leu Leu Gly Ile Gly Ile Leu Val Leu Leu
                 20                  25                  30

Ile Ile Val Ile Leu Gly Val Pro Leu Ile Ile Phe Thr Ile Lys Ala
             35                  40                  45

Asn Ser Glu Ala Cys Arg Asp Gly Leu Arg Ala Val Met Glu Cys Arg
         50                  55                  60

Asn Val Thr His Leu Leu Gln Gln Glu Leu Thr Glu Ala Gln Lys Gly
 65                  70                  75                  80

Phe Gln Asp Val Glu Ala Gln Ala Ala Thr Cys Asn His Thr Val Met
                 85                  90                  95

Ala Leu Met Ala Ser Leu Asp Ala Glu Lys Ala Gln Gly Gln Lys Lys
                100                 105                 110

Val Glu Glu Leu Glu Gly Glu Ile Thr Thr Leu Asn His Lys Leu Gln
            115                 120                 125

Asp Ala Ser Ala Glu Val Glu Arg Leu Arg Arg Glu Asn Gln Val Leu
        130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
        180

<210> SEQ ID NO 6
<211> LENGTH: 126
<212> TYPE: PRT
<213> ORGANISM: Artificial Sequence
<220> FEATURE:
<223> OTHER INFORMATION: Description of Artificial Sequence: L chain V
      region version a of humanized anti-HM1.24 antibody

<400> SEQUENCE: 6

Met Gly Trp Ser Cys Ile Ile Leu Ser Leu Val Ala Thr Ala Thr Gly
                -15                 -10                  -5

Val His Ser Asp Ile Gln Met Thr Gln Ser Pro Ser Ser Leu Ser Ala
         -1   1              5                   10

Ser Val Gly Asp Arg Val Thr Ile Thr Cys Lys Ala Ser Gln Asp Val
             15                  20                  25

Asn Thr Ala Val Ala Trp Tyr Gln Gln Lys Pro Gly Lys Ala Pro Lys
         30                  35                  40                  45

Leu Leu Ile Tyr Ser Ala Ser Asn Arg Tyr Thr Gly Val Pro Ser Arg
                 50                  55                  60

Phe Ser Gly Ser Gly Ser Gly Thr Asp Phe Thr Phe Thr Ile Ser Ser
                 65                  70                  75
```

```
Leu Gln Pro Glu Asp Ile Ala Thr Tyr Tyr Cys Gln Gln His Tyr Ser
        80                  85                  90

Thr Pro Phe Thr Phe Gly Gln Gly Thr Lys Val Glu Ile Lys
        95                 100                 105

<210> SEQ ID NO 7
<211> LENGTH: 139
<212> TYPE: PRT
<213> ORGANISM: Artificial Sequence
<220> FEATURE:
<223> OTHER INFORMATION: Description of Artificial Sequence: H chain V
      region version r of humanized anti-HM1.24 antibody

<400> SEQUENCE: 7

Met Asp Trp Thr Trp Arg Val Phe Leu Leu Ala Val Ala Pro Gly
            -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30              35                  40                      45

Glu Trp Met Gly Ser Ile Phe Pro Gly Asp Gly Asp Thr Arg Tyr Ser
                 50                  55                  60

Gln Lys Phe Lys Gly Arg Val Thr Met Thr Ala Asp Lys Ser Thr Ser
             65                  70                  75

Thr Ala Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
         95                 100                 105

Trp Gly Gln Gly Thr Thr Val Thr Val Ser Ser
110                 115                 120

<210> SEQ ID NO 8
<211> LENGTH: 139
<212> TYPE: PRT
<213> ORGANISM: Artificial Sequence
<220> FEATURE:
<223> OTHER INFORMATION: Description of Artificial Sequence: H chain V
      region version s of humanized anti-HM1.24 antibody

<400> SEQUENCE: 8

Met Asp Trp Thr Trp Arg Val Phe Leu Leu Ala Val Ala Pro Gly
            -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30              35                  40                      45

Glu Trp Met Gly Ser Ile Phe Pro Gly Asp Gly Asp Thr Arg Tyr Ser
                 50                  55                  60

Gln Lys Phe Lys Gly Arg Val Thr Ile Thr Ala Asp Lys Ser Thr Ser
             65                  70                  75

Thr Ala Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
         95                 100                 105
```

```
-continued

Trp Gly Gln Gly Thr Thr Val Thr Val Ser Ser
110                 115             120
```

ENHANCER FOR ANTIBODY TO LYMPHOCYTIC TUMORS

TECHNICAL FIELD

The present invention relates to an enhancer comprising as an active ingredient a biological response modifier (BRM), for pharmaceuticals for treatment of lymphocytic tumors, comprising an antibody that specifically binds to protein expressed in lymphocytic tumors as an active ingredient.

BACKGROUND ART

Lymphocytic cells are mainly responsible for immunity in organisms. Lymphocytic cells, which are all derived from the same stem cells in the blood, undergo repeated differentiation by the action of various differentiation-inducing factors or growth factors in the bone marrow or other organs, and are then released into the peripheral blood. Based on differences in differentiation, lymphocytic cells are roughly classified into B cells and T cells. It is believed that B cells have the ability of producing antibodies whereas T cells have the ability of presenting antigens, have a cytotoxic ability, and have various other abilities. When cells undergo tumorigenic transformation during the stage of differentiation, and start to grow abnormally in the bone marrow, lymphatic tissues and the peripheral blood, they become what are called lymphocytic tumors.

Because of the recent introduction of new technologies, specifically technological advances using monoclonal antibodies to differentiation antigens on the cell surface, it is now possible to identify the origin and/or the stage of lymphocytic cells. Currently, and for lymphocytic tumors as well, it is now possible to identify not only whether the origin of tumor cells is T cells or B cells but also the degree of maturity.

Based on the origin or the degree of maturity of tumor cells, lymphocytic tumors are roughly classified into the B cell tumors and the T cell tumors. B cell tumors are classified based on the degree of maturity into acute B lymphocytic leukemia (B-ALL), chronic B-lymphocytic leukemia (B-CLL), pre-B lymphoma, Burkitt lymphoma, follicular lymphoma, follicular pallial lymphoma, diffuse lymphoma, myeloma, and the like. T cell tumors are also classified based on the degree of maturity into acute T lymphocytic leukemia (T-ALL), chronic T lymphocytic leukemia (T-CLL), adult T cell leukemia (ATL), non-ATL peripheral T lymphoma (PNTL), and the like (Zukai Rinsho [Gan] (Clinical Illustrated [Cancer]), Series No. 17, Leukemia/Lymphoma, Takashi Sugimura et al., MEDICAL VIEW, 1987, B cell tumors, Kiyoshi Kouzuki, Nishimura Shoten, 1991).

Despite recent progress in medical technology, there is much to be desired in the treatment of lymphocytic tumors. For example, the cure rate of acute lymphocytic leukemia (ALL) is lower than 20%. In the case of lymphoma, the cure rate of B lymphoma is relatively high because of the progress in multiple-drug combination therapy, but the cure rate during the advanced stage is still about 50%. Further, T lymphoma is more refractory with the cure rate being about 30%, and less than 10% in adult T cell leukemia (ATL).

On the other hand, Goto, T. et al. have reported a monoclonal antibody (anti-HM1.24 antibody) that was obtained by immunizing mice with human myeloma cells (Blood (1994) 84, 1922-1930). When anti-HM1.24 antibody was administered to a mouse transplanted with human myeloma cells, the antibody accumulated in tumor tissues in a specific manner (Masaaki Kosaka et al., Nippon Rinsho (Japan Clinical) (1995) 53, 627-635), suggesting that anti-HM1.24 antibody could be applied in the diagnosis of tumor localization by radioisotopic labeling, missile therapies such as radiotherapy, and the like.

On the other hand, cancer patients often have decreased immunological functions. Since this is believed to be associated with carcinogenesis, attempts to improve these functions are being conducted. Biological response modifiers (BRM) serve to lead the direct and/or indirect response power of the organisms to tumors in a direction advantageous to the organisms, and this is used in the treatment. They mainly enhance the functions of macrophages, T cells and the like, and restore immunological ability and the like. In the days of treatment and research using non-specific immunity-activating substances, various cytokines were investigated for their biological activity and those that were found to be potentially effective were produced in large amounts (Konnniti no Tiryoyaku (Therapeutic Drugs of Today) (1995 edition), Yutaka Mizushima and Akimasa Miyamoto ed., Nankodo K.K., the 3rd printing of the 17th edition issued on Jun. 20, 1995).

DISCLOSURE OF INVENTION

Currently employed methods of treating lymphocytic tumors include various chemotherapies, radiotherapy, bone marrow transplantation, and the like. However, none of them, as mentioned above, are perfect, and there is a need for new therapeutic agents or therapeutic methods that remit lymphocytic tumors and prolong the survival time of patients.

Thus, it is an object of the present invention to provide a novel enhancer against lymphocytic tumors.

In attempts to provide such methods of treatment, the inventors of the present invention examined the combined use of anti-HM1.24 antibody (Goto, T. et al., Blood (1994) 84, 1922-1930) and a biological response modifier and found that the combined use results in more potent cytotoxic activity, and revives a normal level of cytotoxic activity especially when the cytotoxic activity has been decreased, suggesting potential anti-tumor effects on lymphocytic tumors, and thereby have completed the present invention.

Thus, the present invention provides an enhancer, for treatment of lymphocytic tumors, for an antibody that specifically binds to protein having the amino acid sequence as set forth in SEQ ID NO: 5 and that has a cytotoxic activity, said enhancer comprising a biological response modifier as an active ingredient.

The present invention also provides an enhancer for a biological response modifier for treatment of lymphocytic tumors, said enhancer comprising, as an active ingredient, an antibody that specifically binds to protein having the amino acid sequence as set forth in SEQ ID NO: 5 and that has a cytotoxic activity.

The present invention also provides the above enhancer wherein the lymphocytic tumors are T cell tumors.

The present invention also provides the above enhancer wherein the lymphocytic tumors are B cell tumors.

The present invention also provides the above enhancer wherein the B cell tumors are myeloma.

The present invention also provides the above enhancer wherein the antibody is monoclonal antibody.

The present invention also provides the above enhancer wherein the cytotoxic activity is ADCC activity.

The present invention also provides the above enhancer wherein the antibody has the constant region Cγ of human antibody.

The present invention also provides the above enhancer wherein the constant region Cγ of human antibody is Cγ1 or Cγ3.

The present invention also provides the above enhancer wherein the antibody is anti-HM1.24 antibody.

The present invention also provides the above enhancer wherein the antibody is chimeric antibody or humanized antibody.

The present invention also provides the above enhancer wherein the antibody is chimeric anti-HM1.24 antibody.

The present invention also provides the above enhancer wherein the antibody is a humanized anti-HM1.24 antibody.

The present invention also provides the above enhancer wherein the antibody specifically binds to an epitope recognized by anti-HM1.24 antibody.

The present invention also provides the above enhancer wherein the biological response modifier is interferon, OK432, lenthinan, sonifilan, pestatin, krestin, N-CWS, levamisole, G-CSF, IL-2, IL-10, or IL-15.

The present invention also provides the above enhancer wherein the antibody has a cytotoxic activity wherein ADCC activity is lower than 25% under the condition of an E/T ratio being 50.

The present invention also provides the above enhancer wherein the ADCC activity is measured by the Cr (chromium) release assay.

The present invention also provides the above enhancer according to any of the above that is used in vivo.

The present invention also provides a therapeutic agent for lymphocytic tumors, said agent comprising an antibody that specifically binds to protein having the amino acid sequence as set forth in SEQ ID NO: 5 and that has a cytotoxic activity, and a biological response modifier.

EMBODIMENT FOR CARRYING OUT THE INVENTION

1. Antibody Preparation 1-1. Hybridoma Preparation

Hybridomas that produce antibodies for use in the present invention can be basically constructed using a known procedure as described below. Thus, HM1.24 antigen protein or cells that express HM1.24 antigen may be used as a sensitizing antigen and immunization is carried out in the conventional method of immunization. The immune cells thus obtained are fused with known parent cells in the conventional cell fusion process, and then screened by the conventional screening method to screen cells that produce monoclonal antibodies.

Specifically, monoclonal antibodies may be obtained in the following manner. For example, as a HM1.24 antigen-expressing cell which is a sensitizing antigen for obtaining antibody, there can be used a human multiple myeloma cell line KPMM2 (Japanese Unexamined Patent Publication (Kokai) No. 7(1995)-236475) or KPC-32 (Goto T. et al., Jpn. J. Clin. Hematol. (1991) 32, 1400). Alternatively, as the sensitizing antigen, there may be used a protein having the amino acid sequence as set forth in SEQ ID NO: 1 or a peptide or polypeptide containing an epitope recognized by anti-HM1.24 antibody.

As used herein, cDNA that encodes a protein having the amino acid sequence as set forth in SEQ ID NO: 5 has been inserted in the XbaI cleavage site of pUC19 vector and thereby has been prepared as the plasmid pRS38-pUC19. *E. coli* having this plasmid has been internationally deposited under the provisions of the Budapest Treaty as *Escherichia coli* DH5α (pRS38-pUC19) on Oct. 5, 1993 with the National Institute of Bioscience and Human Technology, Agency of Industrial Science and Technology, of 1-3, Higashi 1-chome, Tsukuba-shi, Ibaraki, Japan, as FERM BP-4434 (see Japanese Unexamined Patent Publication (Kokai) No. 7(1995)-196694). The cDNA fragment contained in this plasmid pRS38-pUC19 can be used to prepare a peptide or a polypeptide containing an epitope recognized by anti-HM1.24 antibody by a genetic engineering technology.

Preferably mammals to be immunized with the sensitizing antigen are selected in consideration of their compatibility with the parent cell for use in cell fusion. They generally include, but are not limited to, rodents such as mice, rats, hamsters and the like.

Immunization of animals with a sensitizing antigen is carried out using a known method. A general method, for example, involves the intraperitoneal or subcutaneous administration of a sensitizing antigen to the mammal.

Specifically, a sensitizing antigen which has beendiluted and suspended in an appropriate amount of phosphate buffered saline (PBS) or physiological saline etc. is mixed, as desired, with an appropriate amount of Freund's complete adjuvant. After being emulsified, it is preferably administered to a mammal several times every 4 to 21 days. Alternatively a suitable carrier may be used at the time of immunization of the sensitizing antigen.

After immunization and the confirmation of the increase in the desired antibody levels in the serum, the immune cells are taken out from the mammal and are subjected to cell fusion. The preferred immune cells include in particular the spleen cells.

The mammalian myeloma cells as the other parent cells which are subjected to cell fusion with the above-mentioned immune cells preferably include various known cell lines such as P3X63Ag8.653) (J. Immunol. (1979) 123: 1548-1550), P3X63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), FO (de St. Groth, S. F. et al., J. Immunol. Methods (1980) 35: 1-21), S194 (Trowbridge, I. S., J. Exp. Med. (1978) 148: 313-323), R210 (Galfre, G. et al., Nature (1979) 277: 131-133) and the like.

Cell fusion between the above immune cells and the myeloma cells may be essentially conducted in accordance with a known method such as is described in Milstein et al. (Kohler, G. and Milstein, C., Methods Enzymol. (1981) 73: 3-46) and the like.

More specifically, the above cell fusion is carried out in a conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance the efficiency of the fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture and, besides, a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v) and mixed to obtain the desired fusion cells (hybridomas). Then by repeating the sequential addition of a suitable culture liquid and centrifugation to remove the supernatant, cell fusion agents etc. which are undesirable for the growth of the hybridoma can be removed.

Said hybridoma is selected by culturing in the conventional selection medium, for example, the HAT culture medium (a culture liquid containing hypoxanthine, aminopterin, and thymidine). Culturing in said HAT culture medium is continued generally for a period of time sufficient to effect killing of the cells other than the desired hybridoma (non-fusion cells), generally several days to several weeks. The conventional limiting dilution method is conducted in which the hybridomas that produce the desired antibody are screened and monclonally cloned.

In addition to obtaining the above hybridoma by immunizing an animal other than the human with an antigen, it is also possible to sensitize human lymphocytes in vitro with HM1.24 antigen or HM1.24 antigen-expressing cells, and the resulting sensitized lymphocytes are fused with a myeloma cell for example U266, to obtain the desired human antibody having the activity of binding to HM1.24 antigen or HM1.24 antigen-expressing cells (see Japanese Post-examined Patent Publication (Kokoku) No. 1(1989)-59878). Furthermore, a transgenic animal having a repertoire of all human antibody genes can be immunized with the antigen, i.e., HM1.24 antigen or HM1.24 antigen-expressing cells, to obtain the desired humanized antibody in the method described above (see International Patent Application WO 93-12227, WO 92-03918, WO 94-02602, WO 94-25585, WO 96-34096 and WO 96-33735).

The monoclonal antibody-producing hybridomas thus constructed can be subcultured in the conventional culture liquid, or can be stored for a prolonged period of time in liquid nitrogen.

In order to obtain monoclonal antibodies from said hybridoma, there can be mentioned a method in which said hybridoma is cultured in the conventional method and the antibodies are obtained as the supernatant, or a method in which the hybridoma is administered to and grown in a mammal compatible with said hybridoma and the antibodies are obtained as the ascites. The former method is suitable for obtaining high-purity antibodies, whereas the latter is suitable for a large scale production of antibodies.

Specifically the anti-HM1.24 antibody-producing hybridoma can be constructed using: the method of Goto, T. et al. (Blood (1994) 84: 1922-1930). It can be conducted by a method in which the anti-HM1.24 antibody-producing hybridoma that was internationally deposited under the provisions of the Budapest Treaty as FERM BP-5233 on Sep. 14, 1995 with the National Institute of Bioscience and Human Technology, Agency of Industrial Science and Technology, of 1-3, Higashi 1-chome, Tsukuba-shi, Ibaraki pref., Japan, is intraperitoneally injected to BALB/c mice (manufactured by CLEA Japan) to obtain the ascites from which the anti-HM1.24 antibody is purified, or: a method in which said hybridoma is cultured in a suitable culture medium such as the RPMI1640 medium containing 10% bovine fetal serum and 5% BM-Condimed H1 (manufactured by Boehringer Mannheim), the hybridoma SFM medium (manufactured by GIBCO-BRL), the PFHM-II medium (manufactured by GIBCO-BRL) and the like, and the anti-HM1.24 antibody can be purified from the supernatant.

1-2. Recombinant Antibody

A recombinant antibody which was produced by the recombinant gene technology in which an antibody gene was cloned from the hybridoma and integrated into a suitable vector which was then introduced into a host can be used in the present invention as monoclonal antibody (see, for example, Carl, A. K., Borrebaeck, and James, W. Larrick, THERAPEUTIC MONOCLONAL ANTIBODIES, published in the United Kingdom by MACMILLAN PUBLISHERS LTD. 1990).

Specifically, mRNA encoding the variable region (V) region of the desired antibody is isolated from the hybridoma producing the antibody. The isolation of mRNA is conducted by preparing total RNA using, for example, a known method such as the guanidine ultracentrifuge method (Chirgwin, J. M. et al., Biochemistry (1979) 18, 5294-5299) or the AGPC method (Chomczynski, P. et al., Analytical Biochemistry (1987) 162, 156-159), and then mRNA is purified from the total RNA using the mRNA Purification kit (manufactured by Pharmacia) and the like. Alternatively, mRNA can be directly prepared using the Quick Prep mRNA Purification Kit (manufactured by Pharmacia).

cDNA of the V region of the antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932) that employs polymerase chain reaction (PCR) may be used. The desired DNA fragment is purified from the PCR product obtained and may be ligated to vector DNA. Moreover, a recombinant vector is constructed therefrom and then is introduced into E. coli etc., from which colonies are selected to prepare the desired recombinant vector. The base sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector which already contains DNA encoding the C region of the antibody.

In order to produce the antibody for use in the present invention, the antibody gene is integrated as described below into an expression vector so as to be expressed under the control of the expression regulatory region, for example an enhancer and/or a promoter. Subsequently, the expression vector may be transformed into a host cell and the antibody can then be expressed therein.

1-3. Altered Antibody

In accordance with the present invention, artificially altered recombinant antibodies such as chimeric antibody and humanized antibody can be used for the purpose of lowering heterologous antigenicity against humans. These altered antibodies can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Application WO 96-02576). Using this known method, chimeric antibody useful for the present invention can be obtained.

For example, *E. coli* having the plasmid that contains the L chain V region or the H chain of chimeric anti-HM1.24 antibody has been internationally-deposited under the provisions of the Budapest Treaty as *Escherichia coli* DH5α (pUC19-1.24L-gκ) and *Escherichia coli* DH5α (pUC19-1.24H-gγ1), respectively, on Aug. 29, 1996 with the National Institute of Bioscience and Human Technology, Agency of Industrial Science and Technology, of 1-3, Higashi 1-chome, Tsukuba-shi, Ibaraki, Japan, as FERM BP-5646 and FERM BP-5644, respectively (see International Patent Application WO 98-14580).

Humanized antibody which is also called reshaped human antibody has been made by transplanting the complementarity determining region (CDR) of antibody of a mammal other than the human, for example mouse antibody, into the CDR of human antibody. The general recombinant DNA technology for preparation of such antibodies is also known (see European Patent Application EP 125023 and International Patent Application WO 96-02576).

Specifically, a DNA sequence which was designed to ligate the CDR of mouse antibody with the framework region (FR) of human antibody is synthesized from several divided oligonucleotides having sections overlapping with one another at the ends thereof. The oligonucleotides are then synthesized into one integrated DNA. The DNA thus obtained is ligated to the DNA encoding the C region of human antibody and then is integrated into an expression vector, which is introduced into a host for antibody production (see European Patent Application EP 239400 and International Patent Application WO 96-02576).

For the FR of human antibody ligated through CDR, the complementarity determining region that forms a favorable antigen binding site is selected. When desired, amino acids in the framework region of the antibody variable region may be substituted so that the complementarity determining region of reshaped human antibody may form an appropriate antigen biding site (Sato, K. et al., Cancer Res. (1993) 53, 851-856).

For example, *E. coli* having the plasmid that contains the L chain a version and the H chain r version of humanized anti-HM1.24 antibody has been internationally deposited under the provisions of the Budapest Treaty as *Escherichia coli* DH5α (pUC19-RVLa-AHM-gκ) and *Escherichia coli* DH5α (pUC19-RVHr-AHM-gγ1), respectively, on Aug. 29, 1996 with the National Institute of Bioscience and Human Technology, Agency of Industrial Science and Technology, of 1-3, Higashi 1-chome, Tsukuba-shi, Ibaraki, Japan, as FERM BP-5645 and FERM BP-5643, respectively (International Patent Application WO 98-14580). Furthermore, *E. coli* having the plasmid containing the s version of the H chain has been internationally deposited under the provisions of the Budapest Treaty as *Escherichia coli* DH5α (pUC19-RVHs-AHM-gγ1) on Sep. 29, 1997 with the National Institute of Bioscience and Human Technology, Agency of Industrial Science and Technology, of 1-3, Higashi 1-chome, Tsukuba-shi, Ibaraki, Japan, as FERM BP-6127.

The amino acid sequence and the nucleotide sequence of each of the V region of the L chain a version of humanized anti-HM1.24 antibody, the H chain r version of humanized anti-HM1.24 antibody, and the H chain s version of humanized anti-HM1.24 antibody are shown in SEQ ID NO: 2, 3, and 4. Amino acids at positions −15 to −1 are of a signal sequence.

For chimeric antibody or humanized antibody, the C region of human antibody is used, and as the C region of human antibody that exhibits cytotoxic activity, human Cγ, for example Cγ1, Cγ2, Cγ3, and Cγ4 can be used. Among them, antibody having Cγ1 and Cγ3 in particular has potent cytotoxic activity i.e. ADCC activity and CDC activity and is used preferably in the present invention.

Chimeric antibody consists of the variable region of antibody derived from a mammal other than the human and the C region derived from human antibody, whereas humanized antibody consists of the complementarity determining region of antibody derived from a mammal other than the human and the framework region (FR) and the C region of antibody derived from human antibody. Accordingly, antigenicity thereof in the human body has been reduced so that they are useful as the active ingredient of the therapeutic agents of the present invention.

A preferred embodiment of the humanized antibody for use in the present invention includes humanized anti-HM1.24 antibody (see International Patent Application WO 98-14580).

1-4. Expression and Production

Antibody genes constructed as described above may be expressed and obtained in a known method. In the case of mammalian cells, expression may be accomplished using an expression vector containing a commonly used useful promoter, the antibody gene to be expressed, and DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Nature (1979) 277, 108) when SV40 promoter/enhancer is used, or by the method of Mizushima et al. (Nucleic Acids Res. (1990) 18, 5322) when HEF1α promoter/enhancer is used.

In the case of *E. coli*, expression may be conducted by operably linking a commonly used useful promoter, a signal sequence for antibody secretion, and the antibody gene to be expressed, followed by expression thereof. As the promoter, for example, there can be mentioned lacz promoter and araB promoter. The method of Ward et al. (Nature (1098) 341, 544-546; FASEB J. (1992) 6, 2422-2427) may be used when lacz promoter is used, and the method of Better et al. (Science (1988) 240, 1041-1043) may be used when-araB promoter is used.

As the signal sequence for antibody secretion, when produced in the periplasm of *E. coli*, the pelB signal sequence (Lei, S. P. et al., J. Bacteriol. (1987) 169, 4379) can be used. After separating the antibody produced in the periplasm, the structure of the antibody is appropriately refolded before use (see, for example, WO 96-30394).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside transferase (APH) gene, the thymidine kinase (TK) gene, *E. coli* xanthine guaninephosphoribosyl transferase (Ecogpt) gene, the dihydrofolate reductase (dhfr) gene and the like.

For the production of antibody for use in the present invention, any production system can be used. The production systems of antibody preparation comprise the in vitro or the in vivo production system. As the in vitro production systems, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus oocytes*, or (3) insect cells such as sf9, sf21, and Tn5. Known plant cells include, for example, those derived from the genus *Nicotiana*, more specifically cells derived from *Nicotiana tabacum*, which is subjected to callus culture. Known fungal cells include yeasts such as the genus *Saccharomyces*, more specifically *Saccharomyces cereviceae*, or filamentous fungi such as the genus *Aspergillus*, more specifically *Aspergillus niger*.

When the prokaryotic cells are used, there are the production systems which employ bacterial cells. Known bacterial cells include *Escherichia coli* (*E. coli*), and *Bacillus subtilis*.

By introducing, via transformation, the gene of the desired antibody into these cells and culturing the transformed cells in vitro, the antibody can be obtained. Culturing is conducted by known methods. For example, as the culture liquid, DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal and the like.

As further in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). As insects, silkworms can be used.

When plants are used, tabacco, for example, can be used.

Antibody genes are introduced into these animals or plants, and the antibodies are produced in such animals or plants, and recovered. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat borne to the goat who received the embryo or offsprings thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Susumu, M. et al., Nature (1985) 315, 592-594). Moreover, when tabacco is used, the desired antibody gene is inserted into an expression vector for plants, for example PMON 530, and then the vector is introduced into a bacterium such as *Agrobacterium tumefaciens*. The bacterium is then infected to tabacco such as *Nicotiana tabacum* to obtain the desired antibody from the leaves of the tabacco (Julian, K.-C. Ma et al., Eur. J. Immunol. (1994) 24, 131-138).

When antibody is produced in vitro or in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector and the host is transformed therewith (see International Patent Application WO 94-11523).

The antibody produced as described above can be bound to various molecules such as polyethylene glycol (PEG) for use as a modified antibody. "Antibody" as used herein includes these modified antibodies. In order to obtain these modified antibodies, the antibody obtained may be chemically modified. These methods have already been established in the field of the art.

2. Separation and Purification of Antibody 2-1. Separation and Purification of Antibody Antibodies produced and expressed as described above can be separated from the inside or outside of the cell or from the host and then may be purified to homogeneity. Separation and purification of the antibody for use in the present invention may be accomplished by affinity chromatography. As the column used for such affinity chromatography, there can be mentioned Protein A column and Protein G column. Examples of the column employing Protein A column are Hyper D, POROS, Sepharose F.F. and the like.

Alternatively, methods for separation and purification conventionally used for proteins can be used without any limitation. Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like.

2-2. Determination of Antibody Concentration

The concentration of antibody obtained in the above 2-1 can be determined by the measurement of absorbance or by ELISA and the like. Thus, when absorbance measurement is employed, the antibody for use in the present invention or a sample containing the antibody is appropriately diluted with PBS(−) and then the absorbance is measured at 280 nm, followed by calculation using the absorption coefficient of 1.35 OD at 1 mg/ml. When the ELISA method is used, measurement is conducted as follows. 100 µl of goat anti-human IgG (manufactured by BIO SOURCE) diluted to 1 µg/ml in 0.1 M bicarbonate buffer, pH 9.6, is added to a 96-well plate (manufactured by Nunc), and is incubated overnight at 4° C. to immobilize the antibody. After blocking, 100 µl each of appropriately diluted antibody of the present invention or a sample containing the antibody, or 100 µl of human IgG of a known concentration as the standard is added, and incubated at room temperature for 1 hour. After washing, 100 µl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

3. FCM Analysis

Reactivity of the antibody of the present invention with lymphocytes may be examined by flow cytometry (FCM) analysis. As the cells, established cell lines or freshly isolated cells can be used. As established cell lines, there may be used T cell lines such as RPMI8402 (ATCC CRL-1995), acute lymphoblastic leukemia-derived CCRF-CEM (ATCC CCL 119), acute lymphatic leukemia-derived HPB-ALL (FCCH1018), T lymphoma-derived HPB-MLT (FCCH1019), acute lymphatic leukemia-derived JM (FCCH1023), acute lymphoblastic leukemia-derived MOLT-4 (ATCC CRL 1582), acute lymphatic leukemia-derived Jurkat (FCCH1024), acute lymphoblastic leukemia-derived CCRF-HSB-2 (ATCC CCL 120.1), adult T cell leukemia-derived MT-1 (FCCH1043), and Lennert lymphoma-derived KT-3 (Shimizu, S. et al., Blood (1988) 71, 196-203), B cell lines such as EB virus-transformed cells CESS (ATCC TIB 190), EB virus-positive B cells SKW 6.4 (ATCC TIB 215), B lymphoma-derived MC116 (ATCC CRL 1649), acute lymphoblastic leukemia-derived CCRF-SB (ATCC CCL 120), acute myelogenic leukemia patient-derived B cell RPMI 6410 (RCCH6047), Burkitt lymphoma-derived Daudi (ATCC CCL 213), Burkitt lymphoma-derived EB-3 (ATCC CCL 85), Burkitt lymphoma-derived Jijoye (ATCC CCL 87), and Burkitt lymphoma-derived Raji (ATCC CCL 86), and furthermore non-T, non-B cell lines such as acute myelogenic leukemia-derived HL-60 (ATCC CCL 240), acute monocytic leukemia-derived THP-1 (ATCC TIB 202), hystiocytic lymphoma-derived U-937 (ATCC CRL 1593), chronic myelogenic leukemia-derived K-562 (ATCC CCL 243), myeloma-derived RPMI8226 (ATCC CCL 155), myeloma-derived U266B1 (ATCC TIB 196), myeloma-derived KPMM2, myeloma-derived KPC-32, and plasmacytoma-derived ARH-77 (ATCC CRL 1621).

After washing the above cells in PBS(−), 100 µl of antibody or a control antibody diluted to 25 µg/ml in the FACS buffer (PBS(−) containing 2% bovine fetal serum and 0.05% sodium azide) is added thereto, which is then incubated on ice for 30 minutes. After washing with the FACS buffer, 100 µl of 25 µg/ml FITC-labeled goat anti-mouse antibody (GAM, manufactured by Becton Dickinson) is added thereto, which is then incubated on ice for 30 minutes. After washing with the FACS buffer, the cells are suspended in 600 µl of 1 ml of the FACS buffer, and each cell may be measured for its fluorescence intensity using the FACScan (manufactured by Becton Dickinson).

4. Cytotoxic Activity

4-1. Measurement of ADCC Activity

The antibody for use in the present invention is one which has, for example, an ADCC activity as the cytotoxic activity.

According to the present invention, the ADCC activity on lymphatic tumors can be measured in the following manner. First, mononuclear cells are isolated as the effector cells from human peripheral blood or bone marrow by the gravity centrifuge method.

As the target cells (Target cell: T), RPMI8226 (ATCC CCL 155), CCRF-CEM (ATCC CCL 119), (ATCC CCL 120.1), HPB-MLT (FCCH1019), EB-3 (ATCC CCL-85), MC116 (ATCC CRL 1649), CCRF-SB (ATCC CCL 120), K-562 (ATCC CCL 243) or the like is labeled with $^{51}$Cr to be prepared as the target cells. Subsequently, to the labeled target cells is added the antibody to be measured for the ADCC activity and incubated. Effector cells at a suitable ratio to the target cells are then added and incubated.

After the incubation, the supernatant is removed and measured for radioactivity using a gamma counter, whereupon 1% NP-40 can be used for measurement of a maximum free radioactivity. The cytotoxic activity (%) can be calculated as (A−C)/(B−C)×100, in which A is radioactivity (cpm) liberated in the presence of the antibody, B is radioactivity (cpm) liberated by NP-40, and C is radioactivity (cpm) liberated by the medium alone containing no antibody.

4-2. Enhancement of Cytotoxic Activity

In order to exhibit a cytotoxic activity such as an ADCC activity, it is preferred to use Cγ, in particular Cγ1 and Cγ3 as the constant region (C region) of antibody in humans. Furthermore, a more potent ADCC activity or CDC activity can be induced by adding, altering, or modifying part of the amino acids in the C region of antibody.

By way of example, there can be mentioned the construction of an IgM-like polymer of IgG by amino acid substitution (Smith, R. I. F. & Morrison S. L. BIO/TECHNOLOGY (1994) 12, 683-688), the construction of an IgM-like polymer of IgG by amino acid addition (Smith, R. I. F. et al., J. Immunology (1995) 154, 2226-2236), the expression of a tandemly-ligated gene encoding L chain (Shuford, W. et al., Science (1991) 252, 724-727), the dimerization of IgG by amino acid substitution (Caron, P. C. et al., J. Exp. Med. (1992) 176, 1191-1195, Shopes, B., J. Immunology (1992) 148, 2918-2922), the dimerization of IgG by chemical modification (Wolff, E. A. et al., Cancer Res. (1993) 53, 2560-2565), and the introduction of the effector function by altering an amino acid(s) in the hinge region of antibody (Norderhaug, L. et al., Eur. J. Immunol. (1991) 21, 2379-2384) and the like. These can be accomplished by means of the oligomer site-specific mutagenesis using a primer, the addition of a base sequence using a restriction enzyme cleavage site, and the use of a chemical modifier that creates a covalent bond.

5. Subject of Treatment

The present invention provides an enhancer, for treatment of lymphocytic tumors, of antibody that specifically binds to protein having the amino acid sequence as set forth in SEQ ID NO: 1 and that has a cytotoxic activity, said enhancer comprising, as an active ingredient, a biological response modifier. Although the subject of treatment is human patients with common lymphatic tumors, it became clear, as described in the Example below, that the present invention can be applied to human patients having a decreased immunological function. "Decreased immunological function" as used herein means that a cytotoxic activity such as ADCC is decreased.

Specifically, it is especially advantageous when cytotoxic activity in which ADCC activity below 25% is only found under the condition of an E/T ratio being 50. The ADCC activity below 25% is found when immunological functions are decreased by the administration of anti-cancer agents and the like. When the above ADCC activity is measured, the culture time (incubation time) is preferably 4 hours. As a method of determining ADCC activity, the Cr (chromium) release assay or the trypan blue staining method is preferred.

6. Biological Response Modifiers

A biological response modifier (BRM) contained as an active ingredient in the present invention is a substance that has an activity of activating immunity. As a biological response modifier, any compound may be used as long as it attains the effect of the present invention. Preferred examples of biological response modifiers include interferon, OK432, lenthinana, Sonifilan, pestatin, krestin, N-CWS, levamisole, G-CSF, IL-2, IL-10, IL-12, or IL-15 (Konnnitino Tiryoyaku (Therapeutic Drugs of Today) (1995 edition), Yutaka Mizushima and Akimasa Miyamoto ed., Nankodo K.K., 3rd printing of the 17th ed. issued on Jun. 20, 1995; Cytokine 94—Kisokara Saishin Johomade (Cytokine 94—From Basic to Latest Information), Shinpei Kasakura ed., Nihon Igaku-kan K.K., First ed., Jul. 14, 1994; Zusetsu Rinsho [Gan] (Clinical Illustrated [Cancer]), Series No. 19, (Progress in Cancer Clinics), Gan to Menneki (Cancer and Immunity) (New edition), Medical View K.K., Second ed. (New edition) issued on Aug. 31, 1993). Among them, IL-2 is specifically preferred.

These biological response modifiers are substances that act on effector cells and thereby activate the cytotoxic activity of the effector cells in the cytotoxic reaction. These biological response modifiers may be prepared by known methods and they are commercially available.

7. Route of Administration and Pharmaceutical Preparation

The enhancers of the present invention may be administered, either systemically or locally, by a parenteral route, for example intravenous injection such as drip infusion, intramuscular injection, intraperitoneal injection, and subcutaneous injection. The method of administration may be chosen, as appropriate, depending on the age and the condition of the patient. The effective dosage is chosen from the range of 0.01 mg to 100 mg per kg of body weight per administration. Alternatively, the dosage in the range of 1 to 1000 mg, preferably 5 to 50 mg per patient may be chosen. For the biological response modifiers, the dosage is chosen from the range of 1 unit to 1,000,000 units per administration.

In accordance with the present invention, a biological response modifier enhancing the action of antibody that specifically binds to protein having the amino acid sequence as set forth in SEQ ID NO: 1 and having a cytotoxic activity may be administered either before or after the administration of said antibody to the subject of treatment, for example human patients with tumor, as long as it enhances the action of the antibody. Alternatively, it can be administered simultaneously with said antibody.

In accordance with the present invention, said antibody and the biological response modifier may not only be given to human patients with tumors but be used for ex vivo treatment. Thus, after effector cells are extracted from the patient's peripheral blood and then the immunological functions thereof are activated with a biological response modifier, the effector cells are returned to the patient. The antibody may be administered before or after or simultaneously as the effector cells are returned to the patient. The present invention may also used for the apheresis of PBSCT (transplantation of stem cells from the peripheral blood). Thus, in PBSCT, said antibody and biological response modifier may be given when the extracted stem cells are returned.

The present invention encompasses the embodiments as described above as long as the combined use of said antibody and the biological response modifier enhances the action thereof.

The enhancers of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used may be chosen from, but not limited to, the above or combinations thereof depending on the dosage form.

The subject diseases of treatment of the present invention are lymphocytic tumors in which an antigen to which the antibody for use in the present invention binds on the target tumor cell. Specifically, multiple myeloma, acute B lymphocytic leukemia (B-ALL), chronic B lymphocytic leukemia (B-CLL), pre-B lymphoma, Burkitt lymphoma, follicular lymphoma, follicular pallial lymphoma, diffuse lymphoma, acute T lymphocytic leukemia (T-ALL), chronic T lymphocytic leukemia (T-CLL), adult T cell leukemia (ATL), non-ATL peripheral T lymphoma (PNTL), and the like. The enhancers of the present invention are useful as enhancers for the treatment of these lymphocytic tumors.

EXAMPLES

The present invention will now be explained hereinbelow in more detail with reference to the following examples. It is to be noted, however, that the present invention is not limited to these examples in any way.

Example

Measurement of ADCC Activity

ADCC (Antibody-dependent Cellular Cytotoxicity) activity was measured according to the method as set forth in Current Protocols in Immunology, Chapter 7, Immunologic studies in humans, Editor, Johan E, Coligan et al., John Wiley & Sons, Inc., 1993.

1. Preparation of Effector Cells

Monocytes were separated from the peripheral blood or bone marrow of healthy humans and patients with multiple myeloma by the density centrifugation method. Thus, an equal amount of PBS(-) was added to the peripheral blood and the bone marrow of healthy humans and patients with multiple myeloma, which was layered on Ficoll (manufactured by Pharmacia) Conrey (manufactured by Daiichi Pharmaceutical Co. Ltd.) (specific gravity, 1.077), and was centrifuged at 400 g for 30 minutes. After the monocyte layer was collected, and washed twice with RPMI 1640 (manufactured by Sigma) supplemented with 10% bovine fetal serum (manufactured by Witaker) 500 U/ml of IL-2 (manufactured by Genzyme), 20 ng/ml of IL-10 (manufactured by Genzyme), 20 ng/ml of IL-12 (manufactured by R & D), 20 ng/ml of IL-15 (manufactured by Genzyme), or 5000 U/ml of M-CSF (manufactured by Gree Cross K.K.) was added or was not added (medium only) to the cells and cultured for 3 days. After washing each culture twice with the same culture medium, the cells were prepared at a cell density of $5 \times 10^6$/ml with the same culture liquid.

2. Preparation of Target Cells

The human myeloma cell line RPMI 8226 (ATCC CCL 155) was radiolabeled by incubating in the RPMI 1640 (manufactured by Sigma) supplemented with 10% bovine fetal serum (manufactured by Witaker) together with 0.1 mCi of $^{51}$Cr-sodium chromate at 37° C. for 60 minutes. After radiolabeling, cells were washed three times with Hanks balanced salt solution (HBSS) and adjusted to a concentration of $2\times10^5$/ml.

3. ADCC Assay

Into a 96-well U-bottomed plate (manufactured by Corning) were added 50 μl of $2\times10^5$ target cells/ml, 1 μg/ml of affinity-purified humanized anti-HM1.24 antibody, or control human IgG (manufactured by Serotec), and reacted at 4° C. for 15 minutes.

Then, 100 μl of $5\times10^5$ effector cells/ml was added thereto, and cultured in the $CO_2$ incubator for 4 hours, whereupon the ratio (E:T) of the effector cells (E) to the target cells (T) was set at 50:1.

One hundred μl of the supernatant was taken and the radioactivity released into the culture supernatant was measured by a gamma counter (ARC361, manufactured by Aloka). For measurement of the maximum radioactivity, 1% NP-40 (manufactured by BRL) was used. Cytotoxicity (%) was calculated by (A−C)/(B−C)×100, wherein A is radioactivity (cpm) released in the presence of antibody, B is radioactivity (cpm) released by NP-40, and C is radioactivity (cpm) released by the culture liquid alone without antibody.

Figure 1:
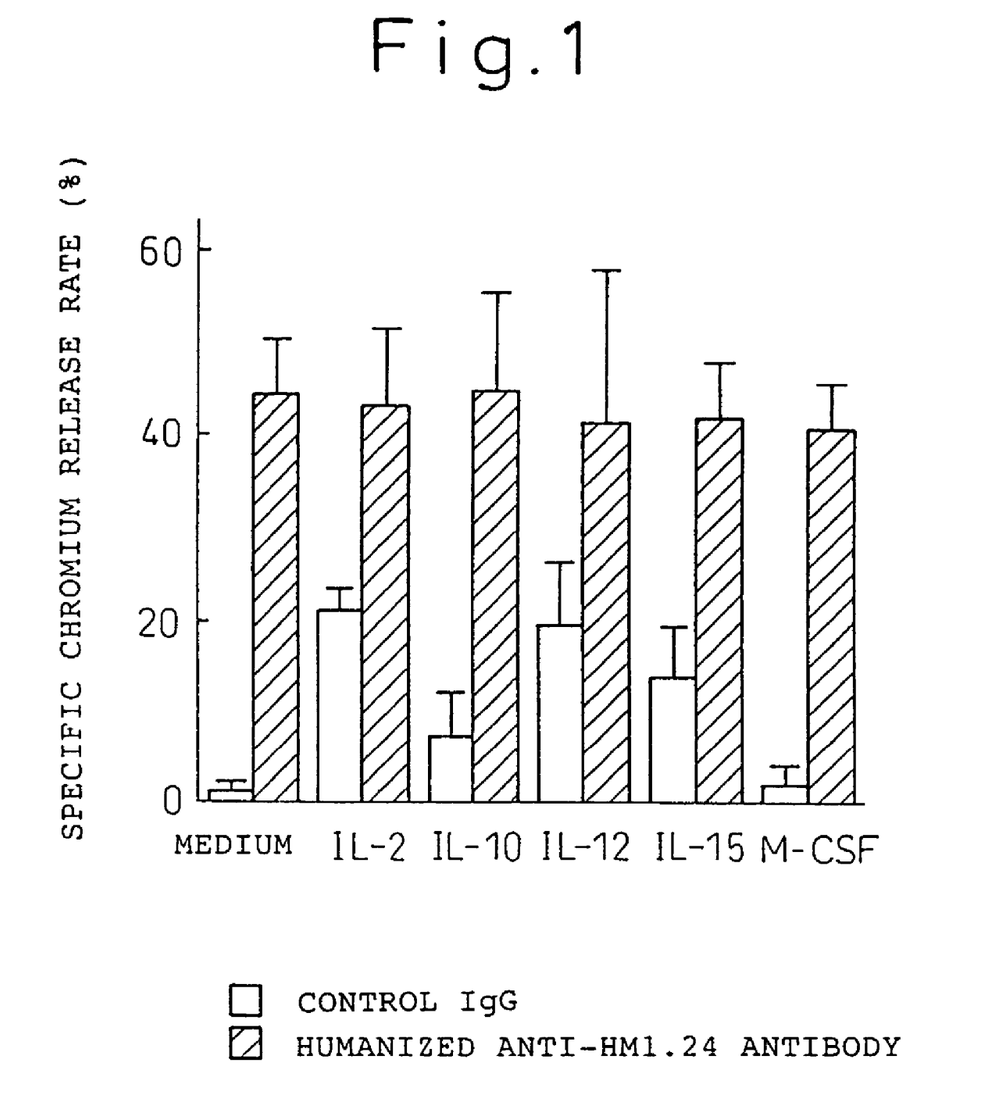
FIG. 1 is a graph showing that humanized anti-HM1.24 antibody exhibits a potent cytotoxic activity on RPMI8226 cells when cells derived from the peripheral blood of healthy humans are used as effector cells.
Figure 2:
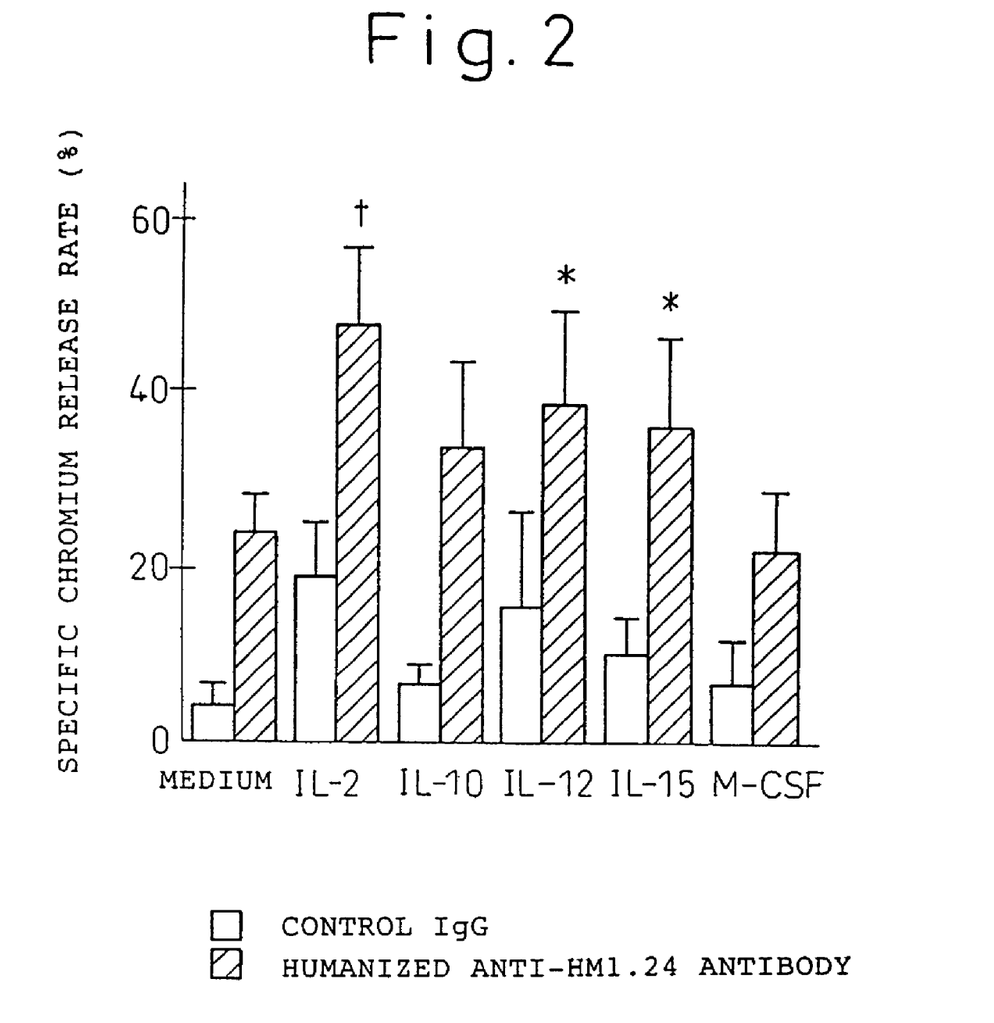
FIG. 2 is a graph showing that humanized anti-HM1.24 antibody exhibits a cytotoxic activity on the RPMI8226 cells when cells derived from the peripheral blood of patients with myeloma are used as effector cells.

As a result, when cells derived from the peripheral blood of healthy humans were used as the effector cell, humanized anti-HM1.24 antibody exhibited a potent cytotoxic activity on the RPMI8226 cells whereas control IgG exhibited almost no cytotoxic activity (FIG. 1). When cells derived from patients with multiple myeloma having decreased immunological functions were used as the effector cell, humanized anti-HM1.24 antibody exhibited a cytotoxic activity on the RPMI8226 cells whereas control IgG exhibited almost no cytotoxic activity (FIG. 2).

However, the activity was weaker than those for the above healthy humans (less than 25%). When IL-2, IL-10, IL-12, or IL-15 was added thereto, the cytotoxic activity of humanized anti-HM1.24 antibody was enhanced. For IL-2 in particular, the activity was enhanced to the level almost equal to those for the healthy humans (FIG. 2).

Figure 3:
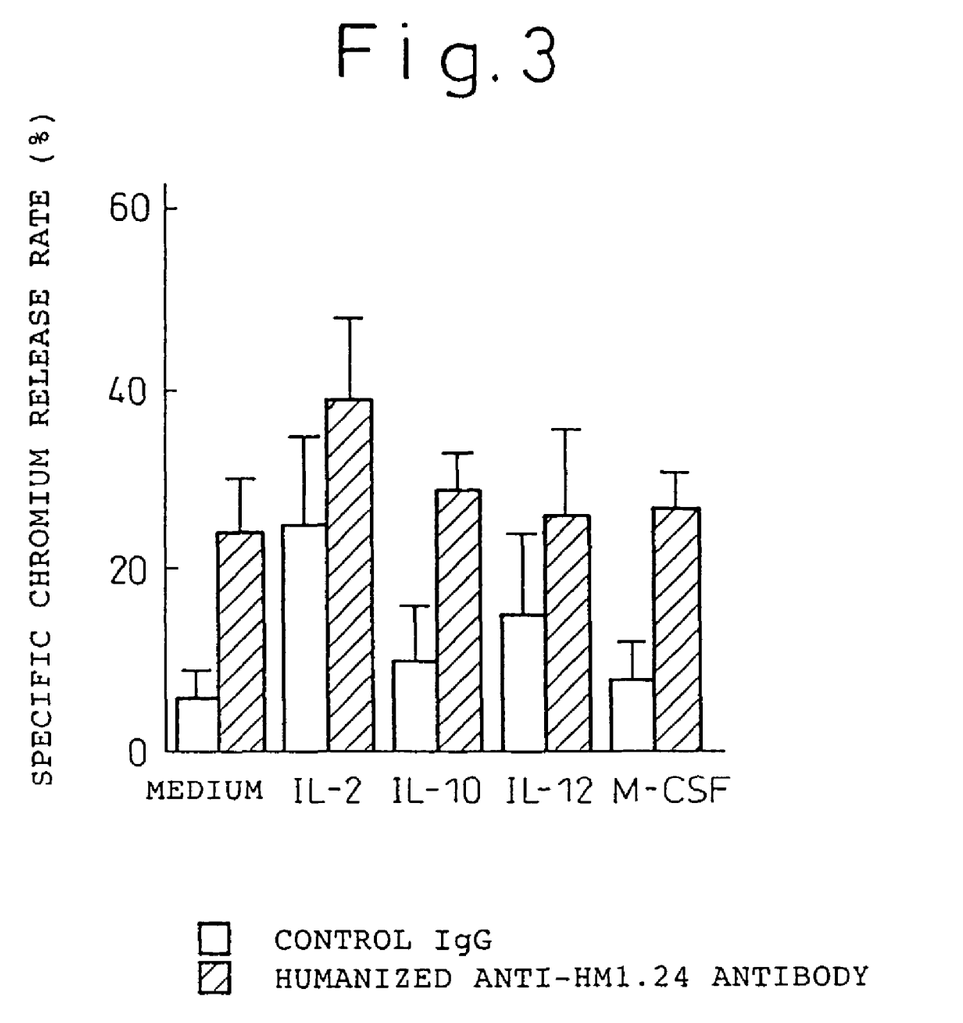
FIG. 3 is a graph showing that humanized anti-HM1.24 antibody exhibits a cytotoxic activity on the RPMI8226 cells when cells, that were subjected to apheresis, from myeloma patients treated with a large dose of cyclophosphamide are used as effector cells.

Further, when cells that were subjected to apheresis from myeloma patients treated with a large dose of cyclophosphamide were used as effector cells, humanized anti-HM1.24 antibody exhibited a cytotoxic activity on the RPMI8226 cells whereas control IgG exhibited almost no cytotoxic activity (FIG. 3). However, the activity was weaker than those for the above healthy humans (less than 25%). When IL-2, IL-10, or IL-12 was added thereto, the cytotoxic activity of humanized anti-HM1.24 antibody was enhanced (FIG. 3).

This indicates that the cytotoxic activity of humanized anti-HM1.24 antibody on the tumor cells that are effector cells derived from patients having decreased immunological functions is weaker than the effector cells derived from healthy humans or patients whose immunological functions are not decreased. By adding BRM such as IL-2, the cytotoxic activity of the effector cells could be enhanced, even to the level of healthy humans.

Thus, when humanized anti-HM1.24 antibody is administered in vivo or ex vivo to patients having decreased immunological functions, the combined use of BRM is expected to further enhance the anti-tumor effects. Similarly, when humanized anti-HM1.24 antibody is administered in vivo or ex vivo to patients to whom cells subjected to apheresis at the time of the transplantation of peripheral blood stem cells etc. are returned, the combined use of BRM is expected to further enhance anti-tumor effects.

Reference Example 1

Preparation of Hybridomas that Produce Mouse Anti-HM1.24 Monoclonal Antibody

In accordance with the method of Goto, T. et al., Blood (1994) 84, 1992-1930, hybridomas that produce mouse anti-HM1.24 monoclonal antibody were prepared.

A plasma cell line KPC-32 ($1\times10^7$ cells) derived from the bone marrow of a patient with human multiple myeloma (Goto, T. et al., Jpn. J. Clin. Hematol. (1991) 32, 1400) was injected twice to the abdominal cavity of a BALB/c mouse (manufactured by Charles River) every six weeks.

Three days prior to sacrificing the animal, $1.5\times10^6$ KPC-32 was injected to the spleen of the mouse in order to further enhance the antibody-producing ability of the mouse (Goto, T. et al., Tokushima J. Exp. Med. (1990) 37, 89). After sacrificing the animal the spleen was extracted and the extracted organ was subjected to cell fusion with the myeloma cell SP2/0 according to the method of Groth, de St. & Schreidegger (Cancer Research (1981) 41, 3465).

By the Cell ELISA (Posner, M. R. et al., J. Immunol. Methods (1982) 48, 23) using KPC-32, the culture supernatant of the hybridoma was screened for antibody. $5\times10^4$ KPC-32 was suspended in 50 ml of PBS and then was aliquoted to a 96-well plate (U-bottomed, Corning, manufactured by Iwaki), which was then air-dried at 37° C. overnight. After blocking with PBS containing 1% bovine serum albumin (BSA), the culture supernatant of the hybridoma was added thereto and incubated at 4° C. for 2 hours. Then, peroxidase-labeled anti-mouse IgG goat antibody (manufactured by Zymed) was reacted at 4° C. for 1 hour. After washing, o-phenylene diamine substrate solution (manufactured by Sumitomo Bakelite) was reacted at room temperature for 30 minutes.

Reaction was stopped by adding 2 N sulfuric acid and the absorbance was measured at 492 nm using the ELISA reader (manufactured by Bio-Rad). In order to remove the hybridoma that produce antibodies against human immunoglobulin, the culture supernatant of the positive hybridoma had previously been adsorbed to human serum and the reactivity to other cell lines was screened by ELISA. Positive hybridomas were selected, and their reactivity to various cells were investigated by flow cytometry. The last selected hybridoma clone was cloned twice, was injected to the abdominal cavity of a pristane-treated BALB/c mouse and ascites were obtained therefrom.

Monoclonal antibodies were purified from the ascites of the mouse by ammonium sulfate precipitation and a Protein A affinity chromatography kit (Ampure Pa., manufactured by Amersham). The purified antibodies were labeled with FITC using the Quick Tag FITC biding kit (manufactured by Boehringer Mannheim).

As a result, monoclonal antibodies produced by 30 hybridoma clones reacted with KPC-32 and RPMI 8226. After cloning, the reactivity of the culture supernatant of these hybridomas with other cell lines or peripheral blood mononuclear cells was investigated.

Among them, 3 clones were monoclonal antibodies that specifically reacted with the plasma cell. From among the 3 clones, a hybridoma clone that was most useful for flow cytometry analysis and had a CDC activity to RPMI 8226 was selected and designated as HM1.24. The subclass of the monoclonal antibody produced by this hybridoma was determined by an ELISA using a subclass-specific anti-mouse rabbit antibody (manufactured by Zymed). Anti-HM1.24 antibody had a subclass of IgG2a κ. The hybridoma HM1.24 that produces anti-HM1.24 antibody was internationally deposited under the provisions of the Budapest Treaty as FERM BP-5233 on Sep. 14, 1995 with the National Institute of Bioscience and Human Technology, Agency of Industrial Science and Technology, of 1-3, Higashi 1-chome, Tsukuba city, Ibaraki pref., Japan.

Reference Example 2

Preparation of Humanized Anti-HM1.24 Antibody

Humanized anti-HM1.24 antibody was obtained according to the method described in International Patent Application WO 98-14580.

From the hybridoma HM1.24 prepared in Reference example 1, total RNA was prepared by the conventional method. From this, cDNA encoding the V region of mouse antibody was synthesized and amplified by a polymerase chain reaction (PCR) method and the 5'-RACE method. A DNA fragment containing the gene encoding the mouse V region was obtained and was ligated to each plasmid puC cloning vector and then introduced into competent E. coli cells to obtain an E. coli transformant. The above plasmid was obtained from the transformant. The base sequence of the cDNA coding region in the plasmid was determined in the conventional method, and the complementarity determining region (CDR) of each V region was determined.

In order to construct a vector expressing chimeric anti-HM1.24 antibody, cDNA encoding the V region of each of L chain and H chain of a mouse anti-HM1.24 antibody was inserted to the HEF vector. Furthermore, in order to construct humanized anti-HM1.24 antibody, the V region CDR of a mouse anti-HM1.24 antibody was transplanted to a human antibody by the CDR transplantation method. The L chain of human antibody REI was used as the L chain of human antibody, FR1-3 of the human antibody HG3 was used for the framework region (FR) 1-3 as the H chain of human antibody, and FR4 of the human antibody JH6 was used for FR4. The amino acid in the FR of the H chain V region was replaced so that the CDR-transplanted antibody could form a suitable antigen-binding site.

In order to express the gene of the L chain and the H chain of the thus constructed humanized anti-HM1.24 antibody in a mammalian cell, each gene was separately introduced into the HEF vector to construct a vector that expresses the L chain or the H chain of the humanized anti-HM1.24 antibody, respectively.

By simultaneously introducing these two expression vectors into the CHO cells, a cell line that produces humanized anti-HM1.24 antibody was established. The antigen binding activity and the binding-inhibition activity to human amniotic membrane cell line WISH of humanized anti-HM1.24 antibody obtained by culturing this cell line was investigated by Cell ELISA. The result indicated that humanized anti-HM1.24 antibody has an antigen binding activity equal to chimeric antibody and, for the binding-inhibition activity using a biotinylated mouse anti-HM1.24 antibody as well, it had an activity equal to chimeric antibody or mouse antibody.

Incidentally, E. coli having the plasmid that contains the L chain or the H chain of chimeric anti-HM1.24 antibody has been internationally deposited under the provisions of the Budapest Treaty as Escherichia coli DH5α (pUC19-1.24L-gκ) and Escherichia coli DH5α (pUC19-1.24H-gγ1) on Aug. 29, 1996 with the National Institute of Bioscience and Human Technology, Agency of Industrial Science and Technology, of 1-3, Higashi 1-chome, Tsukuba-shi, Ibaraki, Japan, as FERM BP-5646 and FERM BP-5644, respectively.

Furthermore, E. coli having the plasmid that contains the L chain a version or the H chain r version of humanized anti-HM1.24 antibody has been internationally deposited under the provisions of the Budapest Treaty as Escherichia coli DH5α (pUC19-RVLa-AHM-gκ) and Escherichia coli DH5α (pUC19-RVHr-AHM-gγ1), respectively, on Aug. 29, 1996 with the National Institute of Bioscience and Human Technology, Agency of Industrial Science and Technology, of 1-3, Higashi 1-chome, Tsukuba-shi, Ibaraki, Japan, as FERM BP-5645 and FERM BP-5643, respectively. Furthermore, E. coli having the plasmid that contains the H chain s version of humanized anti-HM1.24 antibody has been internationally deposited under the provisions of the Budapest Treaty as Escherichia coli DH5α (pUC19-RVHs-AHM-gγ1) on Sep. 29, 1997 with the National Institute of Bioscience and Human Technology, Agency of Industrial Science and Technology, of 1-3, Higashi 1-chome, Tsukuba-shi, Ibaraki pref., Japan, as FERM BP-6127.

Reference Example 3

Cloning of cDNA Encoding HM1.24 Antigen Protein

1. Construction of cDNA Library
1) Preparation of Total RNA cDNA encoding HM1.24 antigen protein specifically recognized by mouse anti-HM1.24 antibody was cloned as described below.

From the human multiple myeloma cell line KPMM2, total RNA was prepared according to the method of Chirgwin et al. (Biochemistry, 18, 5294 (1979)). Thus, 2.2×10⁸ KPMM2 was completely homogenized in 20 ml of 4 M guanidine thiocyanate (manufactured by Nacalai Tesque Inc.).

The homogenate was layered on a 5.3 M cesium chloride solution in a centrifuge tube, which was then centrifuged in a Beckman SW40 rotor at 31,000 rpm at 20° C. for 24 hours to precipitate RNA. The RNA precipitate was washed in 70% ethanol and then dissolved in 300 μl of 10 mM Tris-HCl (pH 7.4) containing 1 mM EDTA and 0.5% SDS. Pronase (manufactured by Boehringer) was added thereto to a concentration of 0.5 mg/ml and then was incubated at 37° C. for 30 minutes. The mixture was extracted with phenol and chloroform, and RNA was precipitated with ethanol. The RNA precipitate was then dissolved in 200 μl of 10 mM Tris-HCl (pH 7.4) containing 1 mM EDTA.

2) Preparation of Poly(A)+RNA

Poly(A)+RNA was purified using as a material about 500 μg of the total RNA, prepared as described above, by the Fast Track 2.0 mRNA Isolation Kit (manufactured by Invitrogen) according to the regimen attached to the kit.

3) Construction of cDNA Library

Double stranded cDNA was synthesized using as material 10 μg of the above poly(A)+RNA by the cDNA synthesis kit TimeSaver cDNA Synthesis Kit (manufactured by Pharmacia) according to the regimen attached to the kit, and was further ligated to the EcoRI adapter supplied in the kit using the Directional Cloning Toolbox (manufactured by Pharmacia) according to the regimen attached to the kit. The kination and the restriction enzyme NotI treatment of the EcoRI adapter were carried out according to the regimen attached to the kit. Furthermore, the adapter-added double stranded cDNA having a size of about 500 bp or greater was separated and purified using a 1.5% low melting point agarose gel (manufactured by Sigma) to obtain about 40 µl of adapter-added double stranded cDNA.

The adapter-added double stranded cDNA thus constructed was ligated using pCOS1 vector and T4 DNA ligase (manufactured by GIBCO-BRL) that had previously been treated with restriction enzymes EcoRI and NotI and alkaline phosphatase (manufactured by Takara Shuzo) to construct a cDNA library. The constructed cDNA library was transduced to an *E. coli* strain DH5α (manufactured by GIBCO-BRL) and consequently it was estimated to be an independent clone having a total size of about $2.5 \times 10^6$. The plasmid pCOS1 was constructed by digesting the expression vector HEF-PMh-gγ1 (see International Patent Application WO 92-19759) with EcoRI and SmaI to delete the contained DNA and by ligating thereto EcoRI-NotI-BamHI Adaptor (manufactured by Takara Shuzo).

2. Cloning by the Direct Expression Method

1) Transfection to COS-7 Cells

About $5 \times 10^5$ clones of the above transduced *E. coli* were cultured in a 2-YT medium (Molecular Cloning: A Laboratory Manual, Sambrook et al., Cold Spring Harbor Laboratory Press (1989)) containing 50 µg/ml ampicillin to amplify cDNA, which was subjected to the alkali method (Molecular Cloning: A Laboratory Manual, Sambrook et al., Cold Spring Harbor Laboratory Press (1989)) to recover plasmid DNA from the *E. coli*. The plasmid DNA thus obtained was transfected to COS-7 cells by the electroporation method using the Gene Pulser instrument (manufactured by Bio-Rad).

Thus, 10 µg of the purified plasmid DNA was added to 0.8 ml of the COS-7 cell solution in which the cells had been suspended in PBS at $1 \times 10^7$ cells/ml, and the mixture was subjected to pulses of 1500 V and 25 µFD capacity. After 10 minutes of recovery at room temperature, the electroporated cells were cultured in a DMEM culture medium (manufactured by GIBCO-BRL) containing 10% bovine fetal serum (manufactured by GIBCO-BRL) under the condition of 37° C. and 5% $CO_2$ for 3 days.

2) Preparation of a Panning Dish

A panning dish on which mouse anti-HM1.24 antibody were coated was prepared by the method of B. Seed et al. (Proc. Natl. Acad. Sci. U.S.A., 84, 3365-3369 (1987)). Thus, mouse anti-HM1.24 antibody was added to 50 mM Tris-HCl (pH 9.5) to a concentration of 10 µg/ml. Three milliliters of the antibody solution thus prepared was added to a cell culture dish with a diameter of 60 mm- and was incubated at room temperature for 2 hours. After washing three times in a 0.15 M NaCl solution, PBS containing 5% bovine fetal serum, 1 mM EDTA, and 0.02% $NaN_3$ was added to the dish. After blocking, it was used for the following cloning.

3) Cloning of cDNA Library

The COS-7 cells transfected as described above were peeled off with PBS containing 5 mM EDTA. After washing the cells once in PBS containing 5% bovine fetal serum, they were suspended in PBS containing 5% bovine fetal serum and 0.02% $NaN_3$ to a concentration of about $1 \times 10^6$ cells/ml. The suspension was added to the panning dish prepared as described above and was incubated at room temperature for 2 hours. After gently washing three times in PBS containing 5% bovine fetal serum and 0.02% $NaN_3$, plasmid DNA was recovered from the cells bound to the panning dish using a solution containing 0.6% SDS and 10 mM EDTA.

The recovered plasmid DNA was transduced into *E. coli* DH5α. After amplifying as described above, the plasmid DNA was recovered by the alkali method. The recovered plasmid DNA was transfected into COS-7 cells by the electroporation method to recover plasmid DNA from the cells bound as described above. A similar procedure was repeated once, and the recovered plasmid DNA was digested with restriction enzymes-EcoRI and NotI, thereby confirming the concentration of an insert having a size of about 0.9 kbp. Furthermore, *E. coli* cells in which a portion of the recovered plasmid DNA had been transduced were inoculated to a 2-YT agar plate containing 50 µg/ml of ampicillin. After culturing overnight, plasmid DNA was recovered from a single colony. It was digested with restriction enzymes EcoRI and NotI to obtain a clone p3.19 in which the size of the insert is about 0.9 kbp.

This clone was reacted using the PRISM Dye Terminater Cycle Sequencing kit (manufactured by Perkin Elmer) according to the regimen attached to the kit, and the base sequence was determined using the ABI 373A DNA Sequencer (manufactured by Perkin Elmer). This base sequence and the corresponding amino acid sequence are shown in SEQ ID NO: 1.

INDUSTRIAL APPLICABILITY

By using anti-HM1.24 antibody and a biological response modifier in combination, the cellular activity of, in particular, effector cells having a decreased ADCC activity was enhanced. This indicates that the combined use of anti-HM1.24 antibody and a biological response modifier results in enhancement of anti-tumor effects on lymphocytic tumors.

Reference to the microorganisms deposited under the Patent Cooperation Treaty, Rule 13-2, and the name of the Depository Institute Depository Institute
  Name: the National Institute of Bioscience and Human Technology, Agency of Industrial Science and Technology
  Address: 1-3, Higashi 1-chome, Tsukuba-shi, Ibaraki, Japan Organism (1)
  Name: *Escherichia coli* DH5α (pRS38-pUC19)
  Accession number: FERM BP-4434
  Date deposited: Oct. 5, 1993

Organism (2)
  Name: Mouse-mouse hybridoma HM1.24
  Accession number: FERM BP-5233
  Date deposited: Apr. 27, 1995

Organism (3)
  Name: *Escherichia coli* DH5α (pUC19-RVHr-AHM-gγ1)
  Accession number: FERM BP-5643
  Date deposited: Aug. 29, 1996

Organism (4)
  Name: *Escherichia coli* DH5α (pUC19-1.24H-gγ1)
  Accession number: FERM BP-5644
  Date deposited: Aug. 29, 1996

Organism (5)
  Name: *Escherichia coli* DH5α (pUC19-RVLa-AHN-gκ)
  Accession number: FERM BP-5645
  Date deposited: Aug. 29, 1996

Organism (6)
  Name: *Escherichia coli* DH5α (pUC19-1.24L-gκ)
  Accession number: FERM BP-5646
  Date deposited: Aug. 29, 1996

Organism (7)
  Name: *Escherichia coli* DH5α (pUC19-RVHs-AHM-gγ1)
  Accession number: FERM BP-6127
  Date deposited: Sep. 29, 1997

The invention claimed is:

1. A method of treating lymphocytic tumors expressing HM1.24 antigen in a human patient in need thereof, said patient exhibiting decreased ADCC activity comprising administering to the patient:
   a therapeutically effective amount of an antibody that specifically binds to a protein having the amino acid sequence of SEQ ID NO:5, said antibody comprising a human constant region; and
   a biological response modifier selected from the group consisting of Il-2, G-CSF, Il-10 or Il-15;
   wherein the decreased ADCC activity of the patient is measured in vitro as less than 25% cytotoxicity without the biological response modifier and under conditions of effector cells to target cells in a ratio of 50, and wherein the effector cells are mononuclear cells obtained from the patient.

2. The method according to claim 1 wherein the lymphocytic tumors are T cell tumors.

3. The method according to claim 1 wherein the lymphocytic tumors are B cell tumors.

4. The method according to claim 3 wherein the B cell tumors are myeloma.

5. The method according to claim 1 wherein the antibody is a chimeric anti-HM1.24 antibody that comprises the variable region of the anti-HM1.24 antibody which is produced by the hybridoma deposited as FERM BP-5233.

6. The method according to claim 1 wherein the antibody is a humanized anti-HM1.24 antibody that comprises the variable region comprising CDRs of the anti-HM1.24 antibody which is produced by the hybridoma deposited as FERM BP-5233.

7. The method according to claim 5 wherein the chimeric anti-HM1.24 antibody is a chimeric antibody comprising the H chain encoded in FERM BP-5644 and the L chain encoded in FERM BP-5646.

8. The method according to claim 6 wherein the humanized antibody is a humanized antibody comprising the L chain encoded in FERM BP-5645, and the H chain encoded in FERM BP-5643 or FERM BP-6127.

* * * * *